United States Patent [19]

Kruger

[11] 4,102,883
[45] Jul. 25, 1978

[54] 19,8-LACTONE STEROID DERIVATIVES AND PROCESSES OF PREPARATION THEREOF

[75] Inventor: Gunther Kruger, St. Laurent, Canada

[73] Assignee: Steele Chemicals Co. Ltd., Pointe Claire, Canada

[21] Appl. No.: 703,824

[22] Filed: Jul. 9, 1976

Related U.S. Application Data

[63] Continuation-in-part of Ser. No. 497,724, Aug. 15, 1974, abandoned, which is a continuation-in-part of Ser. No. 215,669, Jan. 5, 1972, Pat. No. 3,849,402.

[30] Foreign Application Priority Data

Jan. 4, 1972 [CA] Canada .................................. 131674

[51] Int. Cl.² ............................................. C07J 71/00
[52] U.S. Cl. ...................... 260/239.55 R; 260/239.57
[58] Field of Search ................. 260/239.55 R, 239.57, 260/239.55 B

[56] References Cited

U.S. PATENT DOCUMENTS

3,849,402   11/1974   Kruger ............................ 260/239.57

Primary Examiner—Elbert L. Roberts
Attorney, Agent, or Firm—McFadden, Fincham & Co.

[57] ABSTRACT

There are provided novel 19,8-lactone and lactol steroids derivatives having the formula

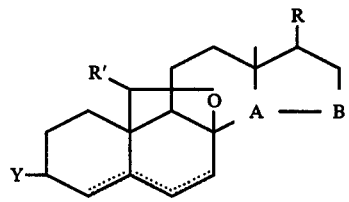

(I)

wherein A and B represent 14- or 15-carbon atoms, respectively, which are either linked by a double bond, or which carry an α- or β-oxido or a 14α- or β-hydroxy group in which case B is a methylene group; Y is =O; 3α or 3β-OH;²H;³H; O-alkyl; or O-acyl; H; R' is OH, =O or acetoxy, the 5-hydrogen atom is either in the α or β-position; there is an optional double bond in position 4(5); 5(6) and 6(7); and R is selected from the group consisting of O-acyl;

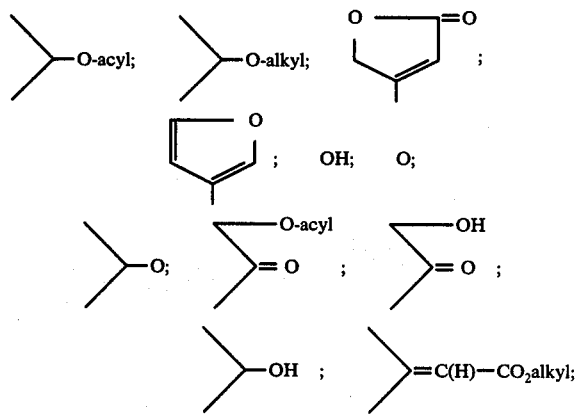

and CN, wherein alkyl is tetrahydropyranyl, lower alkyl, preferably methyl or ethyl, or a substituted methyl wherein the substituent is selected from the group consisting of phenyl, halogen, preferably chlorine and bromine, methoxy, $CH_2$=CH and HC≡C; acyl represents a group selected from those consisting of acetate, trilower-alkyl acetates wherein the lower alkyl group is preferably methyl or ethyl, monohalo acetates and trihalo acetates, preferably wherein the halogen is chlorine and bromine. Several processes for preparing such novel compounds are disclosed, which compounds are useful as intermediates in the preparation of further compounds.

23 Claims, No Drawings

19,8-LACTONE STEROID DERIVATIVES AND PROCESSES OF PREPARATION THEREOF

This application is a continuation-in-part of Ser. No. 497,724, filed Aug. 15, 1974 now abandoned which is a continuation-in-part of Ser. No. 215,669, filed Jan. 5, 1972, now U.S. Pat. No. 3,849,402.

This invention relates to 19,8-lactone steroid derivatives, and to processes for preparing such compounds.

Certain steroidal 19,8-lactones and 19,8-lactols are known in the prior art—for example, as referred to in T. Kubota and G. Ehrenstein, Proceedings of the First International Congress on Hormonal Steroids, 2, 44 (1965), Academic Press, New York, and as well, G. W. Barber and G. Ehrenstein, J. Org. Chem., 26 1230 (1961). These known steroids have no functional groups or centers of unsaturation in position 14 in contrast to the products of the present invention as described hereinafter in greater detail; and previously, these non-14 functionalized compounds have only found use for academic studies. Up to now, processes for preparing such known compounds only resulted in low yields of the products, and used as the starting material the expensive natural product strophanthidin which was converted by degradation processes, involving tedious methods of separation, such as chromotography, into the known products.

With this invention, there have been developed 14-functionalized compounds, which according to one aspect, have the formula

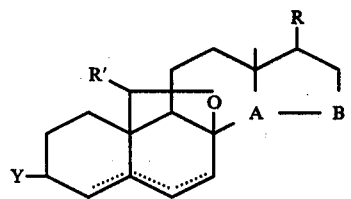

where A and B represent 14- or 15-carbon atoms, respectively, which are either linked by a double bond, or which carry an α- or β-oxido or a 14α- or β-hydroxy group in which case B is a methylene group; Y is =O; 3α or 3β-OH;²H;³H;O-alkyl; O-acyl or H; R' is OH, =O or acetoxy, the 5-hydrogen atom is either in the α or β-position; there is an optional double bond in position 4(5); 5(6) and 6(7); and R is selected from the group consisting of O-acyl;

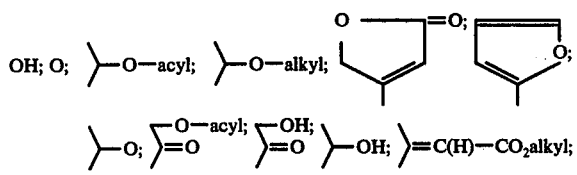

and CN, wherein alkyl is tetrahydropyranyl, 2- or 3-furyl, lower alkyl, preferably methyl or ethyl, or a substituted methyl wherein the substituent is selected from the group consisting of phenyl, halogen, preferably chlorine and bromine, methoxy, CH$_2$=CH and HC≡C; acyl represents a group selected from those consisting of acetate, trilower-alkyl acetates wherein the lower alkyl group is preferably methyl or ethyl, monohalo acetates and trihalo acetates, preferably wherein the halogen is chlorine and bromine or acyl is chosen from 2- or 3-furoate, 2,4,5-trimethyl-, 2,4- or 2,5-dimethylpyrrole-3-carboxylate.

In accordance with the process aspect of the present invention, there is provided a process for preparing the above products of Formula I, which process is selected from the group consisting of (a) oxidizing a compound of the formula

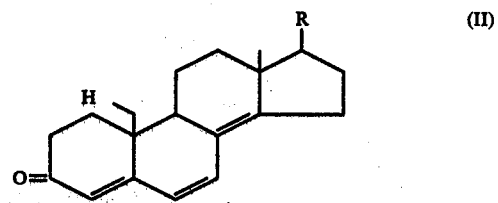

wherein R is as defined above, to form a compound of the Formula I as follows

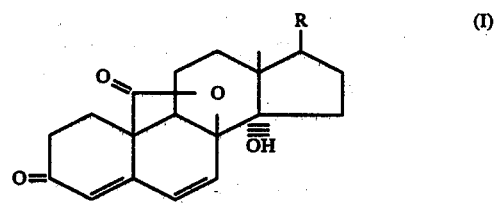

wherein R is as defined above;

(b) epoxidizing a compound of the formula

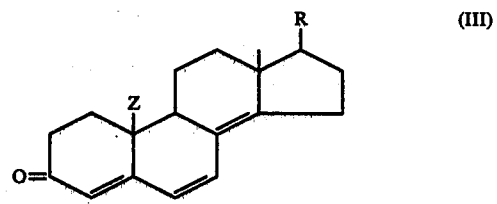

wherein R is as defined above, and Z is O=C—H or O=C—OH, to obtain in the case where Z is the acid group, a compound of the Formula I as follows

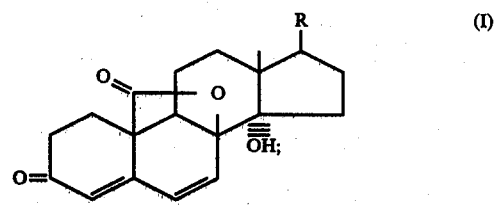

and in the case where Z is the aldehyde group in the compound of Formula III, an intermediate of the formula

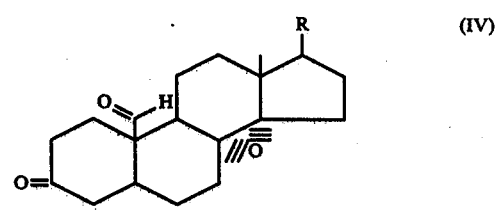

in which R is as defined above, said latter compound of Formula IV is subjected to acid treatment to form a compound of the Formula I as follows

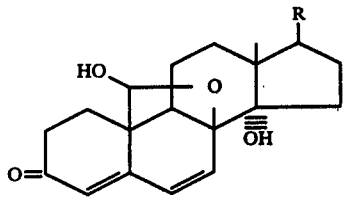

and (c) epoxidizing a compound of the formula

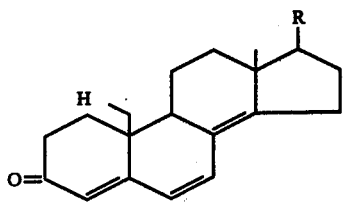

wherein R is as defined above, to form a compound of the formula

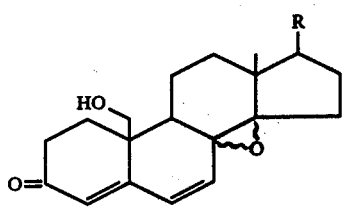

wherein R is as defined above, oxidizing this latter compound to form a compound of the Formula VII

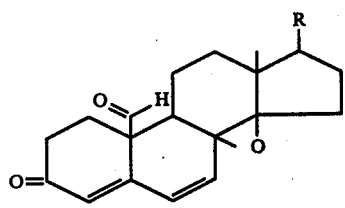

wherein R is as defined above, and subjecting the latter to acid treatment to form a compound of the Formula I as follows

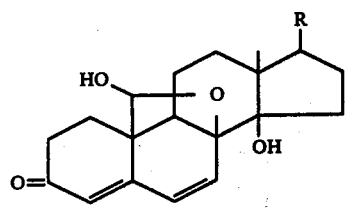

(d) oxidizing a compound of Formula VIa:

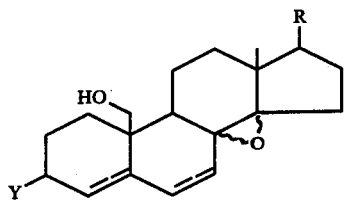

wherein Y and R are as defined above and the dotted lines stand for optional double bonds, to form a compound of the Formula I

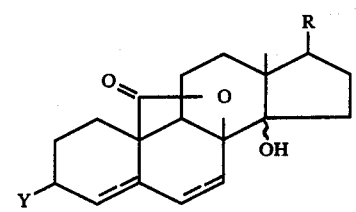

In greater detail of the above processes, and with reference to process (a) above, a compound of the Formula II is oxidized preferably using a combination of $CrO_3$ and sulfuric acid, to yield the compound of the Formula I in which A is an α-hydroxy group attached to the 14-carbon atom and B is a methylene group. Particularly preferred reaction conditions are those similar to the Jones ocidation technique. In this oxidation an intermediate 19-aldehyde of Formula III (wherein Z is the aldehyde group), is formed, as indicated by tlc. Also, the reaction mixture obtained from process (a) is believed to contain the 14β-isomer of the compound of Formula I as produced by this reaction, in addition to a compound of the Formula III, in which Z is the acid group. The minor amount of the 14β-isomer of Formula I produced by this process, and the compound of Formula III in which Z is an acid group, may be separated from the reaction mixture to obtain a pure end product. Separation may be carried out by, for example, extraction of an ethereal solution of the mixture with aqueous base, followed by evaporation, and recrystallization of the residue.

In process (b), and in the embodiment where Z is the aldehyde group in the compound III, the epoxidation to form a compound of the Formula IV is carried out with, for example, a peracid-representative species of which are perbenzoic acid, meta-chlorobenzoic acid, peracetic acid, trifluoroacetic acid, perphthalic acid, etc. The specific reaction conditions may vary—in general, the reaction is preferably carried out at temperatures ranging from about 100° to about −70° C, desirably in a non-polar solvent (i.e. one with a small dielectric constant). Typical solvents include hexane, carbon tetrachloride, benzene, etc. Preferred embodiments of this process include carrying out the reaction at room temperature; in the case where a solvent is employed which does not completely dissolve the starting material, elevated temperatures may then be used.

The compound of the Formula IV may then be subjected to an acid treatment to form a compound of the Formula I, in which A—B is C(α—OH)—$CH_2$ and R' is —OH. The acid treatment may be carried out using any strong acid for this purpose, preferably in a dilute aqueous form. The reaction may be carried out at room temperatures; however, if desired higher or lower temperatures may also be employed. Any suitable strong acid may be employed which will not, under reaction conditions, eliminate the 14-hydroxy group of the resulting end product of Formula I obtained by this reaction. Thus, for example, strong acids such as para-toluenesulfonic acid, methane sulfonic acid, hydrochloric acid, sulfuric acid, etc. may be employed at high dilution. Alternately, the 8α,14α-oxido-19-aldehyde of formula IV may be subjected to Jones oxidation conditions (vide supra) to yield the compound of the formula I in which R' is a carbonyl group (O=).

In process (b), wherein the starting material of the formula III has a carboxylic acid group as the Z substituent, there may be directly obtained a compound of formula I as described above with respect to this reaction. In carrying out this embodiment, the above-described peracids and reaction conditions with respect to the aldehyde compound of formula III may be employed.

With reference to process (c), the starting material of formula II is initially epoxidized by subjecting the latter to treatment with, for example, a peracid; the reaction preferably being carried out in an inert solvent. The peracids and solvents described above with respect to process (b), and the other reaction conditions mentioned thereat, may be employed in this reaction. Preferably, in carrying out this reaction, a high dulution of the solvent to the starting material is employed ranging preferably from 100 to 2000 parts of solvent with respect to the starting material. There is thus obtained as the major product an 8β,14β-oxide of formula V which is accompanied by a minor amount of the corresponding isomeric 8α,14α-oxide and/or the corresponding isomeric 14α-hydroxy-8,19-oxide. Separation of the latter minor products from the 8β,14β-oxide of formula V can, for example, be accomplished by precipitation techniques.

The β-oxide of formula V may then be oxidized to obtain a compound of the formula VI as described above. To this end, the compound of formula V may be oxidized preferably under mild conditions, e.g. with chromium trioxide in pyridine.

In turn, the compound of formula VI may then be converted into the desired end product of formula I (as described above with respect to this process) by subjecting the former to acid treatment. Thus, for example, ethyl acetate-aqueous sulfuric acid may be employed for this purpose to yield a reaction mixture considered to consist essentially of the end product of formula I where R' is OH, A is C(α—OH) and B is a methylene group.

In process (d), a compound of Formula VIa is subjected to oxidation with, for example, chromic acid in the presence sulfuric acid and acetone, in which case the 19-aldehyde of the Formula

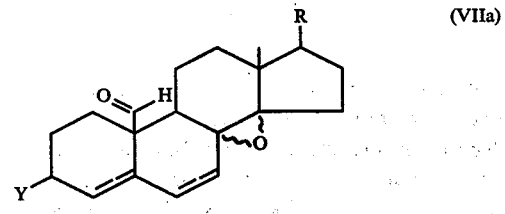

(VIIa)

wherein Y and R are as defined above, is formed as an intermediate.

The various products obtained from the above-described processes (a) through (d) may be converted, if desired, into other novel products of the present invention. Thus, for example, where the products obtained of formula I

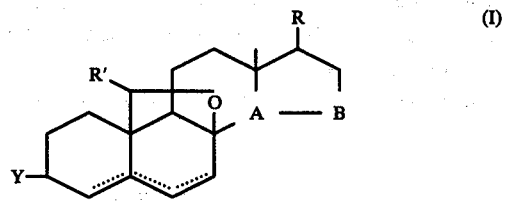

(I)

where R, R', A and B have the above-defined meaning, and Y is keto, this latter group may be reduced to form the corresponding 3-hydroxy compound using, for example, sodium borohydride in the presence of an inert solvent such as methanol. For greater detail of such reduction reactions, reference may be had to Fieser & Fieser Reagents for Organic Synthesis, 1967, page 1049. This 3-keto group may also be eliminated to yield compounds of formula I, in which Y is H. In this case, compounds of formula I, if such compounds have a double bond in the formula in position 4, they are moved to position 3. The step may be effected with zinc and a limited amount of a carboxylic acid—e.g., acetic acid or formic acid, which may optionally contain up to 90% by volume of water. If instead of water, deuterium or tritium oxide is being used, the keto group is replaced by deuterium or tritium, as disclosed in copending application Ser. No. 683,843. Likewise, where the end product of formula I as above, is unsaturated in the 4, 5 and 6 position, the product may be hydrogenated using, for example, palladium on charcoal in a hydrogen atmosphere—for greater detail, reference may be had to Fieser & Fieser (supra) page 778, to yield a compound of formula I fully saturated in the 4, 5 and 6 positions. In this respect, it has been found that when the 3-keto group is reduced to the 3—OH group and if the reduction is carried out before the 4,6-diene hydrogenation process, more of the corresponding 5α-hydrogen steroids of formula I will be obtained, while when the reduction of the 3-keto group is carried out subsequently to the hydrogenation of the double bonds in the 4, 6 position, conversely, more of the corresponding 5β-hydrogen steroids of the formula I will be obtained.

Further, compounds of formula I

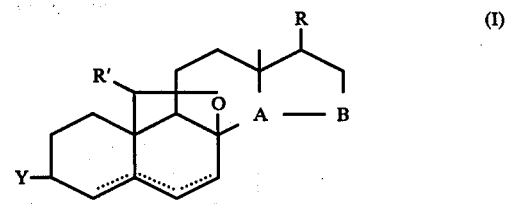

(I)

wherein R, R', Y, A and B are defined as above, may be treated by convert compounds where A is a 14α-OH group to compounds where A—B is a double bond. To this end, the 14α-hydroxy compounds of formula I may be treated with thionyl chloride in pyridine, as for example described in Fieser & Fieser (supra) page 1084. Additionally, for conversion of the products of this invention where A is 14β-OH to other products of this invention, where A—B is a double bond, the above method may also be employed.

The lactol compounds of this invention of formula I, in which R, R', Y, A and B are as defined above, may then be converted to the corresponding lactones by conventional oxidation procedures known to those skilled in this art. Thus, there are obtained lactone compounds of formula I.

These compounds of formula I, which are as follows

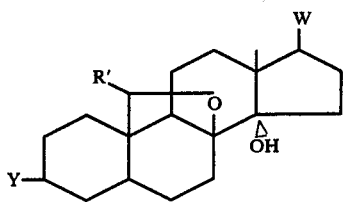

(Ic)

where R' is as defined above and W is a member selected from the group consisting of

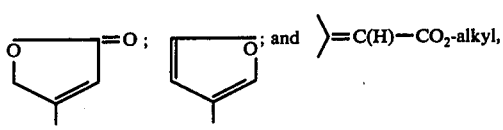

have heart activity as indicated by the well established structure activity relationship established for heart active steroids—see for example W. Eberlein et al., Chem. Ber. Vol. 105, 3686 (1972). Particularly preferred compounds of this category are those in which R' is OH, Y is H and where W is

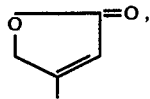

and where the 5 position carries a 5β-H.

In the above compounds of formula (Ic), in which R' is OH, this may be converted to other compounds also having heart activity, as disclosed in my copending application Ser. No. 683,843—such compounds having the formula

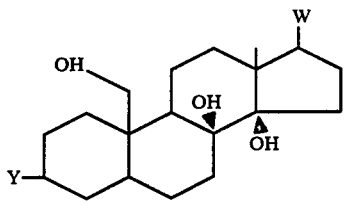

(Id)

where Y and W are as defined above. To this end, such conversion can be, e.g., carried out by using a weak alkali—e.g., aqueous dioxane containing sodium bicarbonate with a water soluble hydrite—e.g., NaBH₄ to yield a compound of the formula (due to the action of the base)

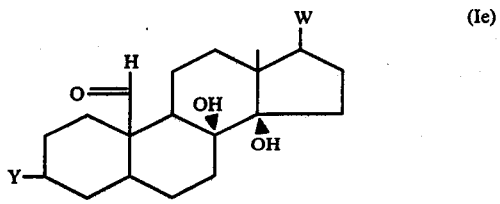

(Ie)

where Y and W are as defined above. In place of the above basic reducing system, pyridine and NaBH₄ may be used.

In addition to the above, an alternate method for converting certain 19,8-lactones of formula (Ic), in which W is

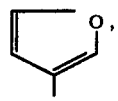

Y is =O, R' is =O, where there is a double bond in the 4 position with an optional double bond in the 6(7) position, the compounds may also be converted to other heart active compounds, as disclosed in copending application Ser. No. 683,843 by treating such compounds with a base—e.g. KOH to initially form compounds of the formula

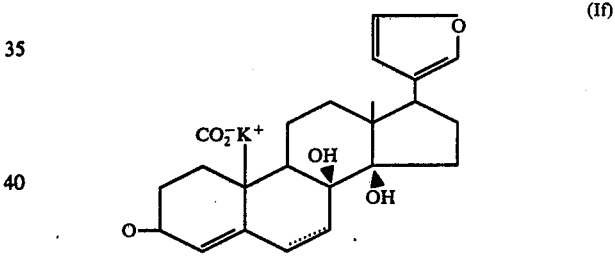

(If)

which may then be decarboxylated at elevated temperatures to yield

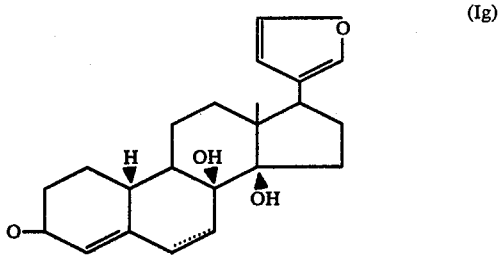

(Ig)

In turn, formula (Ig) may be oxidized to the corresponding cardenolide or the iso-cardenolide by known techniques, and such cardenolides may then be selectively catalytically hydrogenated to yield the corresponding saturated 3-ketones (which may be deoxygenated as per copending application Ser. No. 683,843).

Further other compounds of Formula I of this invention, and where A is 14β-OH, Y is as defined above, R' is =O and R is

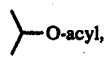—O-acyl, may be used to form other compounds of formula I in which R is

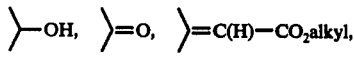

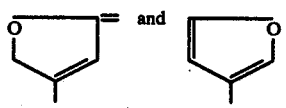

To this end, the end products of formula I are treated successively with alkali (e.g. KOH in methanol) and acid (e.g. dilute HCl in methanol) to yield the 20-alcohol of formula (Ih)

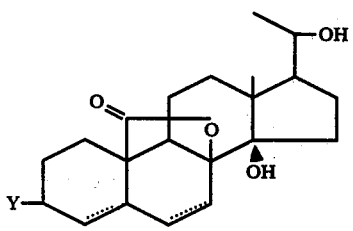

(Ih)

It is to be noted that during the alkali treatment, the lactone ring may be opened by hydrolysis but it will reclose after the acid treatment. Subsequently, the compounds of formula (Ih) may be oxidized to the corresponding 20-ketone compounds by, e.g. as described in copending application Ser. No. 497,729 for the corresponding 14β-OH-8,19-oxido-20-one compounds.

Conversion of the ketone into the corresponding unsaturated ester of formula I where R =

and subsequently to the butenolide ring may be effected by, e.g., the method of F. Sondheimer, Chemistry in Britain, Vol. 1, No. 10, pp. 454–464 (1965). The 19,8-lactone cardenolides of formula I this obtained, where R is

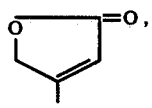

may then be converted to the compounds of formula I where R is

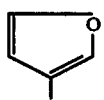

using conventional methods known to those skilled in this art.

In the case of the compounds of the present invention of formula I, which are the lactols, in which R' is OH or the corresponding acetates, this can be made, for example, of a compound of the formula

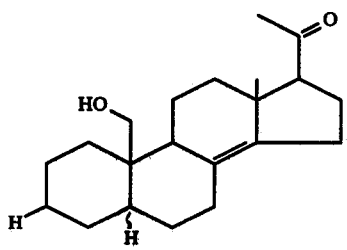

(Ii)

which may be epoxidized to the corresponding 8β,14β-oxide as described previously, to form the corresponding lactol after oxidation of the 19-hydroxy group as also described previously. There is thus obtained a compound of formula I(j)

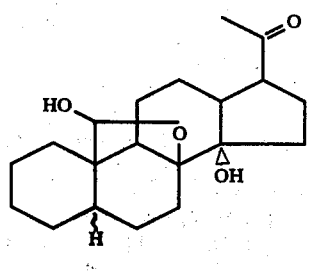

(Ij)

where R is

The starting material of formula I(i) used in the formation of the lactol of formula I(j) may also be converted into the corresponding 19-acetate by conventional procedures, and subsequently to the corresponding 21-acetate by, for example, oxidation by lead tetraacetate, by conventional procedures known to those skilled in this art. The 19,21-diacetate obtained may then be epoxidized to afford a mixture of 8β,14β-oxide and the corresponding 8α,14α-oxide. Hydrolysis of the mixture, followed by selective acetylation of the 21-hydroxy group and oxidation, as described above, will then afford a compound of formula

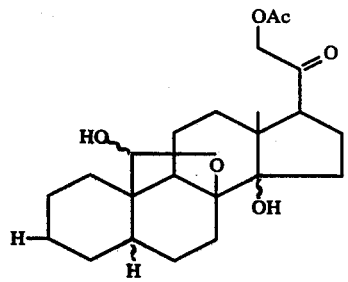

(Ik)

wherein

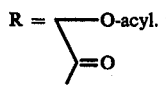

Acetylation of the compound of the formula I(k) will then yield the corresponding compound where R' is O-acyl. This latter compound may then be converted to the corresponding compound wherein R is

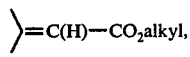

and subsequently to the compound where R is

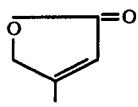

according to the procedures of Sondheimer (supra).

In the case of compound of formula I, wherein R is 17β-acyl, hydrolysis as described above relative to the 20-acetates, where the compounds are the 19,8-lactones, will yield a corresponding 17β-alcohol compound which can be oxidized to the corresponding 17-ketones using the methods employed for the conversion of the corresponding 20-alcohols to the respective 20-ketones, again as described above. The 20-ketones obtained may then be converted to the corresponding 17β-butenolide analogs employing the method of Alfonso as referred to in copending application Ser. No. 516,597.

Still further, in the case of the compounds of formula I of the present invention, in which A and B represent a double bond, and in the case where compounds are the lactols, initially conversion of the lactols to the corresponding lactones is carried out as previously described. Subsequently, the lactones are subjected to hydrogenolysis, employing the methods using for the hydrogenolysis of the corresponding 8,19-oxido-14-ene compounds of copending application Ser. No. 497,730 filed Aug. 15, 1974. There is thus obtained the corresponding 19-carboxylic acids, which of themselves, may be useful for the preparation of the corresponding 19-nor-14β-hydroxycardenolides, the utility of which is outlined in copending application Ser. No. 683,843 filed May 6, 1976. Thus, the compounds of formula I having a 4,6-diene-3-one moiety are particularly useful for this purpose as, after hydrogenolysis to the corresponding 19-carboxylic acid, they may be readily decarboxylated to the corresponding 19-nor-4,6-diene-3-one compounds (as described above). Subsequent hydrogenation of the 4,6-diene moiety and deoxygenation of the resulting saturated 3-ketone (by procedures described above) will then, e.g., in the case of R being

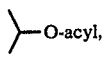

yield a compound of the formula

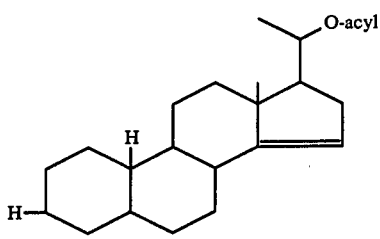

(II)

The above compound of formula I(l), by the procedures described in copending application Ser. No. 516,597, and by other known techniques, will yield a compound of the formula

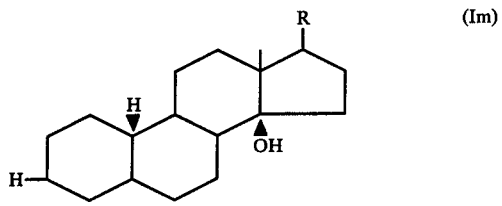

(Im)

wherein R is, e.g.

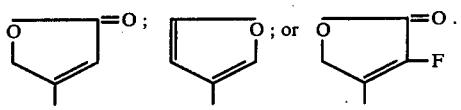

The conversion of the compounds of this invention into the cardenolides, or their analogs, as described above, makes the compounds of this invention very valuable intermediates in the preparation of such cardenolides or their analogs. Such steroid compounds which have a butenolide ring in the 17β-position and a hydroxy group in the 14β-position are well known for the treatment of heart disease. The structure activity relationships indicate that additional groups in the β-position, such as hydroxy groups, and by way of example, the 8β-hydroxy groups found in the compounds obtainable from the compounds of the present invention, increase the heart activity of the 14β-cardenolides. The simple 14β-hydroxy cardenolides derivable from the compounds of the present invention, and which are characterized by not having a 19 carbon atom or a 3-oxygen function, or in the A,B,C,D ring system, are more useful for the establishment of fundamental structure activity relationship than the 14β-hydroxy-cardenolides which in the past have been obtained from natural sources which are complicated by additional functionalities. Reference in this respect may be had to copending application Ser. No. 683,843. However, the compounds of the present invention having the deuterium and the tritium in the 3-position are very valuable for the preparation of simplified 14β-hydroxy-cardenolides, the metabolic fate of which can be readily followed —e.g., the tritiated can be readily followed by analytical methods employing radioactive techniques.

The 19-hydroxy-4,6,8(14)-triene-3-ones of formula IV used as the starting materials for processes (a) and (c) may be obtained from the corresponding known 19-hydroxy-4,6-dien-3-ones (K. Heusler et al., Experiencia, 18, 464 (1962)) by treatment with a strong base in dimethyl sulfoxide and subsequent treatment of the resulting enolate anion with a dehydrogenating agent, e.g. chloranil or 2,3-dichloro-5,6-dicyanoquinone (see copending application Ser. No. 497,691). The 3-oxy-4,6,8(14)-triene-19-als and 19-oic acids of Formula III used as starting material for process (b) may be obtained by oxidation with chromium trioxide in pyridine or in acetone, respectively, as described in application Ser. No. 497,691 filed Aug. 15, 1974 and in the examples hereinafter. In addition, reference may also be had to pending application Ser. No. 215,669 now U.S. Pat. No. 3,849,402 issued Nov. 19, 1974, with respect to the preparation of the starting materials for the 8,14-enes which are saturated in the A and B rings. Copending application Ser. No. 516,597 discloses the preparation of the 3-deoxy-8,14-enes while in copending application Ser. No. 683,843 filed May 6, 1976, the preparation of the same compounds is also disclosed.

For the preparation of compounds of the formula

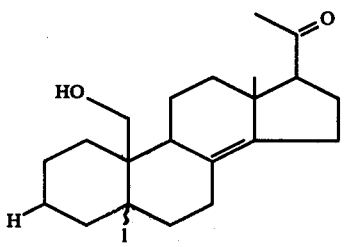

these compounds may be prepared by converting the corresponding 20-acylate (as disclosed in the above copending applications) to the corresponding 19-tetrahydropyranal ether, with subsequent hydrolysis of the 20-acylate to the corresponding alcohol. Oxidation of the latter to the corresponding 20-ketone yields the above compound.

It is a special advantage of process (a) of this invention that there may be obtained, the 14-hydroxy-19:8-lactone compounds of Formula I from the 19-hydroxy-4,6,8(14)-trien-3-one in a single step, and that the lactone formed can be isolated from the reaction mixture by simple methods, such as recrystallization, without taking recourse to elaborate and tedious separation procedures, such as chromatography. It is surprising that under the oxidation conditions employed, the hydroxy lactone and not the corresponding 19-carboxylic acid is formed as the major product, since 4,6-diene-3-one-19-carboxylic acids are formed in high yield when analogous 19-hydroxy-4,6-diene-3-ones are oxidized under the same conditions (see for example, J. Kalvoda, G. Anner Helv., 50, 269(1967).

It is a special advantage of process (b) that in the special epoxidation procedure employed the conversion of the 3-oxo-4,6,8(14)-trien-19-al to the corresponding 3-oxo-8α,14α-oxido-4,6-dien-19-al can be accomplished with a high degree of selectivity, so that the double bonds in position 4 and 6 remain largely unaffected and essentially only the 8α,14α-oxide is obtained. It is a further advantage of the special epoxidation conditions that the labile 8α,14α-oxido-19-aldehyde remains intact until all starting material has been consumed, since when the usual epoxidation conditions were employed (see, for example, L. F. Fieser and M. Fieser, Reagents for Organic Synthesis, John Wiley and Sons, New York, 1967, pp. 136 and 137), the reaction product contained only little of the desired 8α,14α-oxido-4,6-dien-19-al besides numerous by-products.

It is further surprising that in the oxidation of the 3-oxo-8α,14α-oxido-4,6-dien-19-al, instead of the corresponding 19-carboxylic acid, the corresponding 14α-hydroxy-4,6-dien-3-ones 19:8 lactone is formed directly and that the above 8α,14α-oxido 19-aldehyde can be rearranged to the corresponding 14α-hydroxy-19:8-lactol under such mild acidic conditions as brief treatment of the ethereal solution of the latter compound with dilute aqueous hydrochloric acid. Because of this acid-sensitivity of the 3-oxo-8α,14α-oxido-19-al it is the more surprising that this compound can be obtained from the corresponding 3-oxo-4,6,8(14)-trien-19-al by epoxidation, albeit under special conditions, since peracids, such as meta-chloroperbenzoic acid, function as the epoxidizing agents and also yield carboxylic acids during the reaction.

It is similarly of advantage and surprising that the 4,6,8(14)-trien-3-one 19-carboxylic acid of process (b) yields selectively the corresponding 14-hydroxy-4,6-diene lactone when treated under the special epoxidation conditions, under which only the 8(14)-double bond is being oxidized, while the double bonds in position 4 and 6 remain unaffected. It is an advantage of process (c) that it allows the facile preparation of compounds of formula I in which there is a β-hydroxy group in position 14, since, as outlined above, 14β-hydroxy groups are a characteristic feature in the desired end products. It is a special advantage of process (c) that in the epoxidation of the 19-hydroxy-4,6,8(14) trienones predominantly the corresponding 8β,14β-oxidodienones are formed despite the strong steric hindrance of the methyl groups in position 10β and 13β towards the approach of the expoxidizing agent from the β-side. This can be rationalized by considering a cis-directing effect of the 19-hydroxy group which is stronger than the repulsion of the epoxidizing agent by the 10β and 13β-methyl groups. A cis-directing effect of the 19-hydroxy group in the epoxidation of 8(14)-enes has so far not been described; the cis-direction by hydroxy groups in the epoxidation of less hindered hydroxyolefins has been described by, e.g., H. B. Henbest, J. Chem., Soc. (1957) 1958.

It is a common advantage of processes (a), (b) and (c) that they yield products suitable for the conversion into 14-functionalized 19-nor analogs by decarboxylation or decarbonylation since as is well known and for example described in detail in Fieser and Fieser, Steroids, the removal of 19-carbon atoms often brings about a substantial improvement in the physiological activity of steroids.

Having thus generally described the invention, reference will now be made to the following Examples which illustrate preferred embodiments.

EXAMPLE 1

To a stirred mixture of 900 mg of 19-hydroxy-17β-pivaloxyandrosta-4,6,8(14)-trien-3-one and 30 ml of acetone was added 3 ml of chromium trioxide in 8N sulphuric acid. After 40 minutes of stirring, 1.5 ml of additional chromium trioxide in 8 N sulphuric acid was added. After 15 minutes of stirring the reaction was terminated by addition of 1.8 ml of methanol. The mixture was then left to stand for 10 minutes whereafter 900 ml of ether was added. The ethereal phase was extracted three times with 300 ml of water. The aqueous extracts were combined and extracted with ether. The combined ether phases were then extracted twice with 20 ml of water and then four times with 20 ml of KOH-water 1:10. The combined alkaline extracts were extracted with ether and the ethereal phases were combined and dried with sodium sulphate. Evaporation at reduced pressure gave a residue which after several recrystallizations from methylene chloride and ether-petroleum ether gave the purified sample of 8β,14α-dihydroxy-3-oxo-17β-pivaloxyandrosta-4,6-dien-19-oic acid 19,8-lactone, mp 244°–245° C., ir max (KBr) 3320, 3002, 2852, 1780, 1715, 1650, 1615, 1585 and 1170 cm$^{-1}$.

The combined alkaline extracts were acidified with hydrochloric acid-ice 1:10. Extraction with ether followed by drying of the ethereal phase with sodium sulphate and evaporation below 25° C at reduced pressure gave 3-oxo-17β-pivaloxyandrosta-4,6,8(14)-trien-19-oic acid, uv max 343 and 207 mμ, as further evidenced by tlc analysis. Tlc analysis on samples withdrawn from the reaction mixture before the addition of methanol, showed that the first product formed is 3-oxo-17β-pivaloxyandrosta-4,6,8(14)-trien-19-al.

EXAMPLE 2

A mixture of 160 mg of 3-oxo-17β-pivaloxyandrosta-4,6,8(14)-trien-19-al, 160 ml of carbon tetrachloride and 120 mg of metachloroperbenzoic acid was left to stand at room temperature in the absence of light for 16 hours, whereupon an additional 40 mg of metachloroperbenzoic acid was added. The mixture was then left to stand at room temperature for three days whereupon it was extracted three times with 64 ml of 2% aqueous potassium hydroxide and once with 60 ml of water. Drying with sodium sulphate followed by evaporation at reduced pressure below 30° C gave a material which, after several recrystallizations from ether-pentane, gave 37.9 mg of 3-oxo-8α,14α-oxido-17β-pivaloxyandrosta-4,6-dien-19-al, mp 127°–129° C, ir max (KBr) 3015, 2985, 2880, 1730, 1725, 1670, 1620, 1590 and 1160 cm$^{-1}$.

Part of the intermediate fractions obtained during recrystallization of the above product was chromatographed on a thick layer plate, coated with silica gel G, using ethylacetate-benzene 1:4 as the eluent. Oxidation of the purified material with chromic acid in acetone at 0° C by the method described in Example 4 yielded, on dilution of the reaction mixture with ice water filtration and standing of the aqueous phase, a precipitate of 8β,14α-dihydroxy-3-oxo-17β-pivaloxyandrosta-4,6-dien-19-oic acid 19,8-lactone which had an ir-spectrum identical to the lactone prepared according to Example 1.

EXAMPLE 3

A mixture of 50 mg of 3-oxo-20β-pivaloxypregna-4,6-dien-19-al, 50 ml of carbon tetrachloride and 40 mg of metachloroperbenzoic acid was left to stand at room temperature for 66 hours under nitrogen, whereupon it was extracted three times with 30 ml of 2% aqueous potassium hydroxide and once with 50 ml of water. Drying with sodium sulphate followed by evaporation at reduced pressure and addition of hexane gave 26.2 mg of 3-oxo-20β-pivaloxy-8α,14α-oxido-pregna-4,6-dien-19-al, uv max 290 mμ as further verified by tlc analysis and the chemical transformation described in Example 4 below.

EXAMPLE 4

A mixture of 3 mg of 3-oxo-20β-pivaloxy-8α,14α-oxido-pregna-4,6-dien-19-al and 0.375 ml of acetone was cooled externally by an ice bath, whereupon 0.005 ml of chromic acid in 8N sulphuric acid was added, followed by the same amount of oxidising reagent after 5 minutes of stirring. After 40 minutes of stirring, the reaction was terminated by the addition of 0.010 ml of methanol. The mixture was stirred for 5 minutes and 3 ml of ice water was added. Filtration of the resulting precipitate gave 8β,14α-dihydroxy-3-oxo-20β-pivaloxy-pregna-4,6-dien-19-oic acid 19,8-lactone as evidenced by tlc comparison with the 19,8-lactone obtained by the procedure described in Example 5.

EXAMPLE 5

To a mixture of 15 mg of 3-oxo-20β-pivaloxy-8α,14α-oxidopregna-4,6-dien-19-al and 1.5 ml of acetone, which was cooled externally by an ice bath, was added 0.01 ml of chromic acid in 8N sulphuric acid. The mixture was stirred for 32 minutes whereupon 0.015 ml of isopropanol was added. The resulting green precipitate was removed by filtration. The filtrate was concentrated at reduced pressure to approximately one-tenth of its volume and two volumes of water were added. The mixture was left at −5° C for 3 days and was then filtered. Thick layer chromatography on silica gel G coated glass plates gave, on elution with ethylacetate benzene 1:1, two fractions which were recrystallized from ether pentane yielding, as the less polar material, 8β,14α-dihydroxy-3-oxo-20β-pivaloxypregna-4,6,-dien-19-oic acid 19,8-lactone, ir max (KBr) 3499, 2980, 2885, 1770, 1740, 1720, 1670, 1610, 1585 and 1160 cm$^{-1}$, and as the more polar product 14α,19-dihydroxy-8,19-oxido-20β-pivaloxypregna-4,6-dien-3-one (KBr) 3550, 3420 (broad), 1705, 1640, 1610 and 1170 cm$^{-1}$.

EXAMPLE 6

A mixture of 2 mg of 3-oxo-8α,14α-oxido-20β-pivaloxypregna-4,6-dien-19-al, 0.2 ml of ether and 0.2 ml of concentrated hydroxhloric acid-water 1:3 was shaken at room temperature for 3 hours whereupon 3 volumes of water was added. The organic phase was diluted with additional ether and then extracted with water until the washings were neutral. Evaporation at reduced pressure gave a white solid consisting of 14α,19-dihydroxy-8,19-oxido-20β-pivaloxypregna-4,6-dien-3-one as indicated by tlc comparison with the lactol obtained according to the procedure deccribed in the preceding example. Treatment of the compound obtained with an excess of pyridine-acetic anhydride 2:1 at 70° C for 2.5 hours under nitrogen followed by dilution with water, extraction with ether, extraction of the ethereal phase with water and evaporation gave 19-acetoxy-14α-hydroxy-8,19-oxido-20β-pivaloxypregna-4,6-dien-3-one as evidenced by tlc analysis.

EXAMPLE 7

A mixture of 10 mg of 3-oxo-17β-pivaloxyandrosta-4,6,8(14)-trien-19-oic acid, 5 mg of metachloroperbenzoic acid and 0.5 ml of methylene chloride was left standing for 16 hours at room temperature, whereupon it was diluted with ether and extracted with aqueous potassium hydroxide. Evaporation gave a product consisting mainly of 8β,14α-dihydroxy-3-oxo-17β-pivaloxyandrosta-4,6-dien-19-oic acid 19,8-lactone, uv max 283 mμ, and as further verified by tlc analysis. Tlc analysis indicated the presence of another product which was considered to be the isomeric 8β,14β-dihydroxy-3-oxo-17β-pivaloxyandrosta-4,6-dien-19-oic acid 19,8-lactone.

EXAMPLE 8

To a stirred mixture of 1 g. of finely divided 19-hydroxy-20β-pivaloxypregna-4,6,8(14)-trien-3-one in 900 ml of carbon tetrachloride was added a freshly prepared solution of 800 mg of meta-chloroperbenzoic acid in 100 ml of carbon tetrachloride. After some stirring the initially turbid solution became clear; after some further stirring a precipitate formed; after 24 hours of stirring the precipitate was removed by filtration and washed repeatedly with carbon tetrachloride.

The filtrate was extracted 3 times with 2% aqueous potassium hydroxide and once with the same volume of water. It was then dried with sodium sulfate and evaporated at reduced pressure. Recrystallization of the residue obtained with methylene chloride-hexane gave 197.8 mg of 19-hydroxy-8β,14β-oxido-20β-pivaloxypregna-4,6-dien-3-one, mp 167°–168° C. (sintering at 146°), uv (max) 286 mμ, ir (KBr) 3430, 1720, 1660, 1620, 1575, 1280 and 1145 cm⁻¹.

The precipitate, which was obtained after filtration of the reaction mixture, was digested with methanol and methylene chloride to yield 210 mg of 19-hydroxy-8α,1-4α-oxido-20β-pivaloxypregna-4,6-dien-3-one as evidenced by tlc analysis. The latter compound was further characterized as its 19-acetate as described in Example 10.

EXAMPLE 9

A mixture of 60 mg of 19-hydroxy-8β, 14β-oxido-20β-pivaloxypregna-4,6-dien-3-one and 1.5 ml of pyridine was cooled in an ice-bath under dry nitrogen, whereupon 84 mg of anhydrous chromium trioxide was added with stirring. After some stirring a yellow precipitate formed; after some further stirring the mixture turned dark brown. Stirring was then continued without cooling. After 5 hours 0.084 ml of isopropanol was added, followed by 4.5 ml of methylene chloride. The mixture was then filtered through a small column containing approximately 1 g of aluminium oxide. The column was washed with methylene chloride and the filtrate was evaporated at reduced pressure to yield a residue which was dissolved in benzene. Addition of charcoal, followed by filtration through diatomaceous earth, evaporation and recrystallization of the residue obtained with ether-petroleum ether gave 14.2 mg of 3-oxo-8β, 14β-oxido-20β-pivaloxypregna-4,6-dien-19-al, mp 153°–158°, ir (KBr), 1720, 1670, 1620, 1585, 1285, 1220, 1175 and 1135 cm⁻¹.

EXAMPLE 10

A mixture of 10 mg of 19-hydroxy-8α, 14α-oxido-20β-pivaloxypregna-4,6-dien-3-one, 0.2 ml of acetic anhydride and 0.2 ml of pyridine was left to stand under nitrogen at room temperature for 16 hours, whereupon 2.0 ml of water was added. Filtration followed by recrystallization of the precipitate obtained with methylene chloride-hexane gave 19-acetoxy-8α, 14α-oxido-20β-pivaloxypregna-4,6-dien-3-one, ir (KBr) 1740, 1710, 1660, 1625, 1280, 1235 and 1170 cm⁻¹.

EXAMPLE 11

A mixture of 20 mg of 19-hydroxy-8β, 14β-oxido-20β-pivaloxypregna-4,6-dien-3-one, 0.08 ml of pyridine and 0.04 ml of acetic anhydride was left to stand under nitrogen for 16 hours, whereupon 2.4 ml of water was added. After some standing the mixture was extracted with ether and the ethereal solution was extracted several times with water. Evaporation of reduced pressure yielded a resin, which solidified on treatment with pentane. Recrystallisation of the solid from petroleum ether-hexane gave 6.2 mg of 19-acetoxy-8β, 14β-oxido-20β-pivaloxypregna-4,6-dien-3-one, mp 161°–163°, ir (KBr) 1735, 1720, 1670, 1620, 1615, 1285, 1250 and 1170 cm⁻¹.

EXAMPLE 12

A mixture of 16.9 mg of 3-oxo-8β, 14β-oxido-20β-pivaloxypregna-4,6-dien-19-al, 0.338 ml of ethyl acetate and 0.0338 ml of sulfuric acid-water 2:1 was stirred under nitrogen for 100 minutes, whereupon 1.69 ml of ethyl acetate was added and the resulting solution was extracted 6 times with 0.845 ml of water. Evaporation at reduced pressure gave a resin which after digestion with ether-petroleum ether gave a semisolid considered to consist essentially of 14β, 19-dihydroxy-8,19-oxido-20β-pivaloxypregna-4,6-dien-3-one as evidenced by tlc analysis; ir (CHCl₃) 3590, 1715, 1670, 1285, 1165, 1105 and 990 cm⁻¹. A mixture of one half on the latter material, 0.08 ml of acetic anhydride and 0.16 ml of pyridine was left to stand under nitrogen at room temperature for 16 hours, whereupon it was diluted with water. Extraction with ether, followed by extraction of the ethereal solution with water, and evaporation at reduced pressure gave a resin consisting of a mixture of 19-acetoxy-14β-hydroxy-8,19-oxido-20β-pivaloxypregna-4,6-dien-3-one and the isomeric 14α-alcohol as evidenced by tlc-analysis.

EXAMPLE 13

Oxidation of 5 mg of 19-hydroxy-8β, 14β-oxido-20β-pivaloxy-5α-pregnane, which was prepared as described in copending U.S. patent application Ser. No. 710,696 filed Aug. 2, 1976 under conditions which were similar to those described in Example 1 except that in the working up the extraction of the ethereal phase with a base was omitted, gave a crude product which after recrystallisation from ether-pentane yielded 8β, 14β-dihydroxy-20β-pivaloxy-5α-pregnan-19-oic acid 19,8-lactone as a white powder, ir (KBr), 3535, 3500, 3015, 1760, 1739, 1720, 1476, 1460, 1395, 1375, 1282, 1243, 1228, 1204, 1157, 1140, 1124, 1089, 1070, 1042, 1009, 940, 910, 869, 772, 758 and 700 cm⁻¹; m/e 432, 330 (m-102), 312 (m-102-18).

EXAMPLE 14

Oxidation of 20 mg of 19-hydroxy-8β, 14β-oxido-20β-pivaloxy-5β-pregnane, which was prepared as outlined in the copending U.S. patent application Ser. No. 710,696 filed Aug. 2, 1976 under conditions similar to those described in the preceding Example, followed by chromatography of the crude product on silica gel G coated glass plates with ethyl acetate-benzene 1:7 as the eluant gave 9.1 mg of a fraction, which after recrystallisation from ether-pentane yielded 8β, 14β-dihydroxy-20β-pivaloxy-5β-pregnan-19-oic acid 19,8-lactone, mp 258°–259° C., ir (KBr) 3570, 3020, 2996, 2952, 2882, 1770, 1705, 1480, 1445, 1396, 1376, 1284, 1185, 1131, 1059, 1042, 1013, 945, 939, 908, 860, 770 and 760 cm⁻¹; as a white solid. The reaction proceeds via 8β, 14β-oxido-20β-pivaloxy-5β-pregnan-19-al as evidenced by tlc.

I claim:
1. A compound of the formula

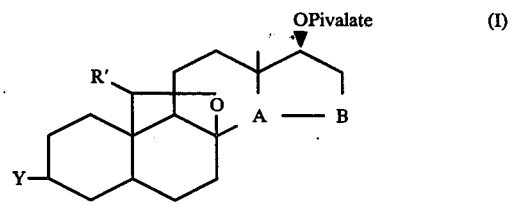

wherein A and B represent 14- and 15-carbon atoms, respectively, which are either linked by a double bond, or which carry an α- or β-oxido or a 14α- or β-hydroxy group in which case B is a methylene group; Y is =O, 3α or 3β-OH, ²H, ³H, O-alkyl, O-acyl or H; R' is OH, =O or acetoxy; the 5-hydrogen atom is either in the α or β position; and the Δ4, Δ5(6) and Δ6 dehydro derivatives thereof.

2. A compound of the formula

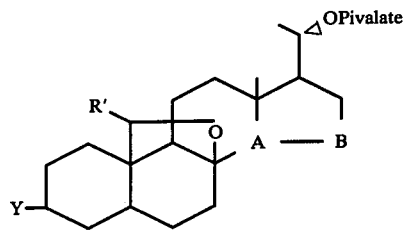
(II)

wherein A and B represent 14- and 15-carbon atoms, respectively, which are either linked by a double bond, or which carry an α- or β-oxido or a 14α- or β-hydroxy group in which case B is a methylene group; Y is =O, 3α or 3β-OH, ²H, ³H, O-alkyl, O-acyl or H; R' is OH, =O or acetoxy; the 5-hydrogen atom is either in the α or β position; and the Δ4, Δ5(6) and the Δ7 derivatives thereof.

3. The compound of claim 2 comprising the 17-acetoxyacetyl derivative thereof.

4. The compound of claim 2 comprising the 17-acetyl derivative thereof.

5. A process for preparing a compound of the formula

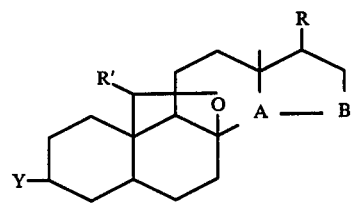

wherein A and B represent 14- or 15-carbon atoms, respectively, which are either linked by a double bond, or which carry an α or β-oxido or a 14α- or β-hydroxy group in which case B is a methylene group; Y is =O, 3α or 3β-OH, ²H, ³H, O-alkyl, O-acyl or H; R' is OH, =O or acetoxy; the 5-hydrogen atom is either in the α or β position, and the Δ4, Δ5(6) and Δ6 dehydro derivatives thereof, and wherein R is selected from the group consisting of 17β-pivalate, the corresponding 17-acetoxyacetyl derivative thereof, the corresponding 17-acetyl derivative thereof, and the 20β-pivalate; which process is selected from the group consisting of (a) oxidizing a compound of the formula

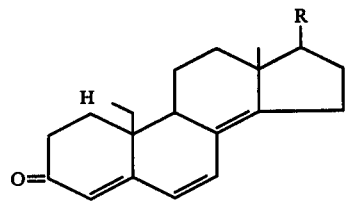
(II)

wherein R is as defined above, to form a compound of the Formula I as follows

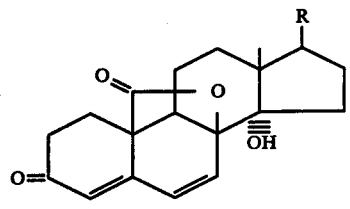
(I)

wherein R is as defined above;

(b) epoxidizing a compound of the formula

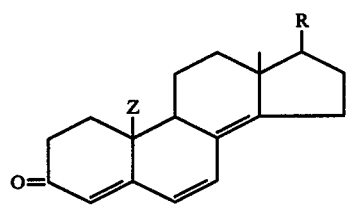
(III)

wherein R is as defined above, and Z is O=C—H or O=C—OH, to obtain in the case where Z is the acid group, a compound of the Formula I as follows

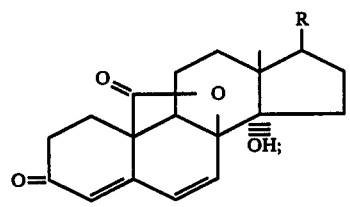
(I)

and in the case where Z is the aldehyde group in the compound of Formula III, an intermediate of the formula

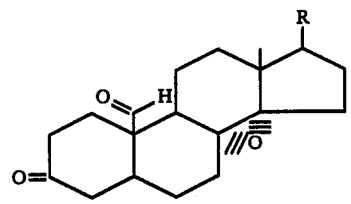
(IV)

in which R is as defined above, said latter compound of Formula IV is subjected to acid treatment to form a compound of the Formula I as follows

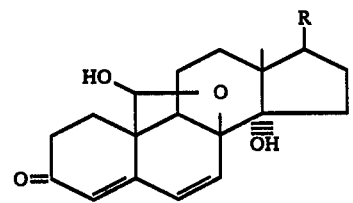
(I)

and (c) epoxidizing a compound of the formula

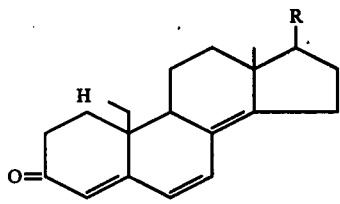

wherein R is as defined above, to form a compound of the formula

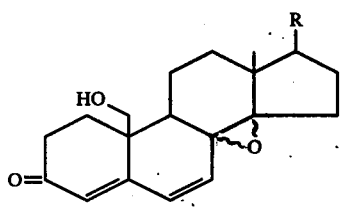

wherein R is as defined above, oxidizing this latter compound to form a compound of the Formula VII

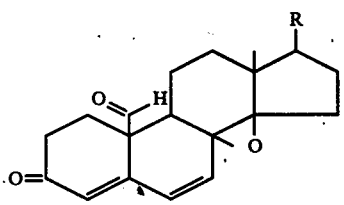

wherein R is as defined above, and subjecting the latter to acid treatment to form a compound of the Formula I as follows

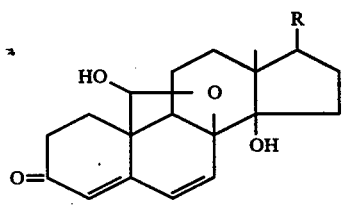

(d) oxidizing a compound of Formula VIa:

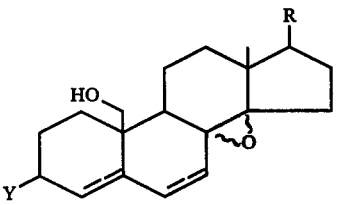

wherein Y and R are as defined above and the dotted lines stand for optional double bonds, to form a compound of the Formula I

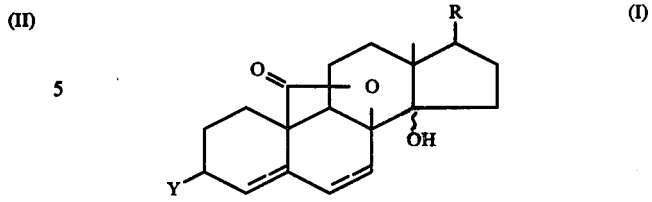

6. A process as defined in claim 5(a) wherein the compound is oxidized using $CrO_3$ and sulphuric acid.

7. A process as defined in claim 5(b) wherein the epoxidation is carried out with a peracid.

8. A process as defined in claim 5(c) wherein the epoxidation is carried out under mild oxidizing conditions, and wherein the acid treatment is carried out using a weak acid.

9. A compound according to claim 1, wherein the substituent Y is chosen from keto, α-hydroxy, β-hydroxy and acetate.

10. A compound according to claim 1, wherein there is included at least one double bond in the 4 or 6 positions.

11. A compound according to claim 1, wherein the substituent A is a 14α or 14β-hydroxy group.

12. A compound according to claim 1, wherein the substituent Y is chosen from H α-hydroxy, β-hydroxy and acetate; and wherein the substituent A is a 14α or 14β-hydroxy group.

13. A method according to claim 2, wherein the substituent Y is chosen from keto, α-hydroxy, β-hydroxy and acetate.

14. A method according to claim 2, wherein the substituent A is a 14α or 14β-hydroxy group, and the substituent B is a methylene group.

15. A compound according to claim 1 wherein the compound is 8β, 14α-dihydroxy-3-oxo-17β-pivaloxyandrosta-4,6-dien-19-oic acid 19,8-lactone.

16. A compound according to claim 2 wherein the compound is 8β, 14α-dihydroxy-3-oxo-20β-pivaloxypregna-4,6-dien-19-oic acid 19,8-lactone.

17. A compound according to claim 2 wherein the compound is 14α, 19-dihydroxy-8,19-oxido-20β-pivaloxypregna-4,6-dien-3-one.

18. A compound according to claim 2 wherein the compound is 19-acetoxy-14α-hydroxy-8,19-oxido-20β-pivaloxypregna-4,6-dien-3-one.

19. A compound according to claim 1 wherein the compound is 8β, 14β-dihydroxy-3-oxo-17β-pivaloxyandrosta-4,6-dien-19-oic acid 19,8-lactone.

20. A compound according to claim 2 wherein the compound is 14β, 19-dihydroxy-8,19-oxido-20β-pivaloxypregna-4,6-dien-3-one.

21. A compound according to claim 2 wherein the compound is 19-acetoxy-14β-hydroxy-8,19-oxido-20β-pivaloxypregna-4,6-dien-3-one.

22. A compound according to claim 2 wherein the compound is 8β-14β-dihydroxy-20β-pivaloxy-5β-pregnan-19-oic acid 19,8-lactone.

23. A compound according to claim 1 wherein the compound is 8β, 14β-dihydroxy-20β-pivaloxy-5α-pregnan-19-oic acid 19,8 lactone.